United States Patent [19]

Friemel et al.

[11] 4,421,742

[45] Dec. 20, 1983

[54] PHOSPHINE PRODUCING PESTICIDE AND METHOD OF MANUFACTURE THEREFOR

[75] Inventors: Wolfgang F. R. Friemel, Heppenheim; Werner O. Praxl, Rimbach, both of Fed. Rep. of Germany

[73] Assignee: Dr. Werner Freyberg Chemische Fabrik Delitia Nachf., Laudenbach, Fed. Rep. of Germany

[21] Appl. No.: 240,447

[22] Filed: Mar. 4, 1981

Related U.S. Application Data

[63] Continuation of Ser. No. 964,410, Nov. 28, 1978, abandoned, which is a continuation-in-part of Ser. No. 850,341, Nov. 19, 1977, abandoned.

[30] Foreign Application Priority Data

Feb. 8, 1977 [DE] Fed. Rep. of Germany ....... 2705228
Dec. 5, 1977 [ZA] South Africa ...................... 77/7233

[51] Int. Cl.$^3$ ..................... A01N 55/00; A01N 59/26
[52] U.S. Cl. .................................... 424/128; 424/184
[58] Field of Search ................................ 424/128, 184

[56] References Cited

U.S. PATENT DOCUMENTS

| | | | |
|---|---|---|---|
| 2,117,158 | 5/1938 | Freyberg et al. | 99/225 |
| 2,793,979 | 5/1957 | Svedres et al. | 424/128 |
| 2,809,916 | 10/1957 | Hermelin | 424/128 |
| 2,826,486 | 3/1958 | Hüter | 71/29 |
| 2,826,527 | 3/1958 | Hüter | 424/128 |
| 2,987,445 | 6/1961 | Leversque | 167/82 |
| 3,132,067 | 5/1964 | Rauscher et al. | 424/128 |
| 3,159,536 | 12/1964 | Marotta | 424/128 |
| 3,179,589 | 4/1965 | Lobos | 252/7 |
| 3,372,088 | 3/1968 | Freyberg et al. | 424/128 |
| 3,624,198 | 11/1971 | Arbaugh | 424/128 |
| 3,719,751 | 3/1973 | Rauscher et al. | 424/27 |
| 4,347,241 | 8/1982 | Kapp | 424/128 |

FOREIGN PATENT DOCUMENTS 888149 12/1971 Canada .
755587 4/1976 South Africa .
824107 10/1959 United Kingdom .

OTHER PUBLICATIONS

Label Registrations Union of South Africa 9 pages 6/26/74.

*Primary Examiner*—Allen J. Robinson
*Attorney, Agent, or Firm*—Millen & White

[57] ABSTRACT

A pesticide composition comprising a particulate hydrolyzable metal phosphide is rendered liquid phase water repellent by treating particles of the composition with a silicon-organic compound. The silicon-organic compound has at least one reactive moiety, preferably hydrogen capable of reacting with and binding to reactive sites contained on surfaces of particles of the composition. Preferably, the reactive group is hydrogen and the reactive site is a hydroxy group. The silicon-organic compound can also undergo cross-linking reactions. In the water-repellent treatment the silicon-organic compound may be applied to and be reacted to become bonded to any of the solid ingredients of the composition, including urea which serves as a self-ignition inhibitor. Preferably at least part of the silicon-organic compound is bonded to particles of the metal phosphide. Advantages result if all the silicon-organic compound is thus bound to the metal phosphide. On the phosphide surfaces novel metal-silicone compounds may form.

The treatment protects the phoshide against access of liquid state water and resulting violent reaction, without inhibiting the access of water in its gaseous state (e.g. atmospheric moisture) required for the generation of phosphine when the composition is used as a fumigant.

The hydrophobing reaction of the silicon-organic compound, e.g. polymethyl hydrogen siloxane is promoted by heat or catalysts (metal organic compounds, bases, e.g. ammonia, ammonium compounds, amines). The composition in powder form (enclosed in gas permeable sachets) or in tablets may contain additives, e.g. self-ignition inhibitors such as ammonium carbamate, ammonium carbonate and urea.

43 Claims, No Drawings

PHOSPHINE PRODUCING PESTICIDE AND METHOD OF MANUFACTURE THEREFOR

CROSS-REFERENCE TO RELATED APPLICATIONS

This is a continuation of application Ser. No. 964,410, filed Nov. 28, 1978, as a continuation-in-part of Ser. No. 850,341, filed Nov. 10, 1977, both now abandoned.

BACKGROUND OF THE INVENTION

The present invention relates to a pesticide which releases hydrogen phosphide (phosphine) upon reaction of a phosphide with water. In particular, this invention relates to a hydrolyzable metal phosphide composition comprising solid matter, treated with a compound which renders the phosphide free to be reached by and react with water in a gaseous state but renders the composition sufficiently repellent to water in a liquid state, to reduce the likelihood of spontaneous ignition.

There are a number of suitable hydrolyzable phosphides commercially available for pesticidal purposes, such as aluminum phosphide, calcium phosphide, and magnesium phosphide, which produce phosphine upon reaction with water. Unfortunately, these phosphides react more or less violently and exothermically on contact with water, especially in the liquid state, and tend to spontaneously ignite the phosphine created thereby. This spontaneous ignition is undesirable in that it becomes a serious fire hazard to materials and/or structures which are being fumigated by the pesticide.

Many attempts have been made to reduce or completely eliminate the tendency of the pesticide and/or products thereof to spontaneously ignite upon reaction with water. The prior art has used additives, such as metallic soaps, paraffin, resins and waxes, to make metal phosphides hydrophobic. Various silicones have also been used for this hydrophobizing purpose. For example, the Federal Republic of West Germany patent application AS No. 1 023 265 (publication date of Jan. 23, 1958) discloses the use of silicone on a phosphide to retard the gaseous escape of phosphine therefrom when the mixture is exposed to moisture. In practice, such a retardation of the release of phosphine is not desired, since humans will not be able to return to the area being fumigated until all phosphine has been released and has had a chance to dissipate therefrom. In addition, some of the prior art coatings maintain the phosphide in an unhydrolyzed state for such long periods of time that the grain or other material being fumigated could contain hazardous phosphide particles long after the fumigation would supposedly be complete. Thus it is desired to have a hydrolyzable phosphide preparation which reacts completely and with relative speed upon interaction with gaseous moisture but repels liquid water therefrom.

Federal Republic of West Germany patent application OS No. 1 542 877 discussed coating the surface of molded bodies, that is tablets, with methyl or phenyl silicone oils to produce the liquid hydrophobizing effect without interfering or impairing the production of the phosphine. However, the silicone oils used in this manner, do not produce the complete liquid phase water repelling effect necessary to insure that spontaneous ignition does not result even when additions of up to about 3% by weight of methyl or phenyl silicone oil are used. Greater amounts than 3% by weight of the silicone oil considerably impair the flowing and pressing properties of the pesticide mixture and limit further normal processing or use.

The other conventional hydrophobizing agents have similar disadvantages to those discussed above. For example, metallic soaps require relatively large amounts thereof to achieve an adequate hydrophobizing effect upon the phosphide. However, large amounts of the hydrophobizing additive limit the use of and inhibit the effectiveness of other important ingredients which are used for suppressing the spontaneous ignition characteristic of such pesticides. In addition, the flowing and pressing properties of such pesticides are also adversely effected by large quantities of these types of hydrophobizing additives. According to U.S. Pat. No. 3,132,067, solid water repellent coating type additives, such as paraffins, synthetic resins, and waxes, preferably in amounts of 4% by weight, are preferably applied in uniform layers upon the phosphide which is frequently difficult to accomplish and normally an extra pretreatment step is required directed toward such additives, such as grinding, melting, dissolving or the like. According to said U.S. Pat. No. 3,132,067 and its prosecution file, such paraffins, synthetic resins and waxes, function to form a relatively strong waterproof coating or shell about the phosphide which is imprevious to water not only in its liquid, but also in its gaseous state. Before reaction can occur with any moisture in any significant amount, this coating must be broken, which according to that patent is accomplished after a delay of several hours from the moment of exposure to the atmosphere by a "bursting" agent which builds up pressure within the shell, thereby breaking the shell and allowing moisture to enter. Problems arise if the composition does not comply with various critical requirements. If the shell rupture is too wide, such a coating will have the disadvantage of allowing liquid water to enter into contact with the phosphide as soon as the shell is broken. In addition, those particles of phosphide which were coated with the hydrophobizing agent but because of poor mixing or other reasons undergo no opening of the shell, may not react with moisture at all during the appropriate time of fumigation and thereby remain in an unreacted state and, thus, present a potentially hazardous situation since the remaining phosphide shells could conceivably be broken open later, thereby releasing the phosphine in the presence of humans or animals. Pesticides with such shells also take a relatively long time after exposure for the release of the phosphine to be substantially complete, even when all of the shells are broken open. As with the previous conventional hydrophobizing agents or additives, relatively large amounts of such waterproofing coatings are normally required and consequently cause the resultant negative processing effects attendant with such large amounts.

OBJECTS AND SUMMARY OF THE INVENTION

Therefore, the principal objects of the present invention are to easily and simply produce a liquid phase water resistant phosphide preparation for use in pest control which easily reacts with and releases phosphine on contact with water in a gaseous state; to provide such a pesticide which utilises an additive which reacts with and binds to the surface of the pesticide particles to provide the desired results; to provide such a pesticide having a relatively low ratio of such additives as compared to the phosphides; to provide such an additive which does not interfere with other ingredients of the pesticide, such as fire retardant blanketing agents; to treat phosphides and phosphide compositions with such an additive which comprises a silicon-organic compound containing silicon atoms and at least one reactive group bound directly to the silicon atom; to provide a method of manufacture of such a pesticide consisting essentially of a metal phosphide and the additive, or a composition including other ingredients such as inert gas releasing blanketing compounds; to provide such a pesticide which does not require a bursting agent; to provide such a pesticide which substantially completes the fumigation process in a relatively short time period; and to provide such a pesticide which is easily used, substantially resistant to spontaneous ignition, economical to produce, and particularly well suited for the proposed usage thereof.

In the present invention particles of a composition comprising solid hydrolyzable phosphide, such as aluminum phosphide, calcium phosphide, magnesium phosphide, or mixtures thereof, have deposited thereon a silicon-organic compound having at least one reactive moiety. Preferably the reactive moiety is hydrogen and the silicon-organic compound completely reacts with and binds to reactive sites which can include cross-linkage reactions between molecules of the said compound and reactions with reactive sites such as hydroxy groups on the particles and in particular on commercial phosphide particles at the point of bonding of the reactive group. The resultant reaction product on the surface of the phosphide provides a barrier to water in the liquid state but allows passage into reactive contact with the phosphide of water in the gaseous state and, thus, allows reaction of this gaseous water with the phosphide. The reaction of the silicon-organic compound with the reactive site is promoted by an elevated temperature, bases, ammonia, ammonium compounds (such as ammonium carbonate, ammonium carbamate) and amines, and selected metallic catalysts (such as organic compounds of lead, zinc, zirconium, tin, cobalt and titanium). Where conditions so require, the pesticide may also include additives, e.g. self-ignition inhibitors such as a blanketing agent (such as ammonium carbonate, ammonium carbamate or mixtures thereof) which releases a fire suppressing gas therefrom or urea. The major portion of the additives, when used, is often added to the phosphide only after the reaction of the reactive sites with the silicon-organic compound is substantially complete; however, when the blanketing agent has catalytic properties, a portion of the blanketing agent may advantageously be added with the initial admixture of the phosphide and the silicon-organic compound thus catalyzing the reaction together thereof. The hydrophobic treatment may be confined substantially to the phosphide particles. However, additives of the composition, e.g. urea, may be hydrophobised by treatment with the silicon-organic compound, and the resulting hydrophobic properties imparted to such additives may then contribute to the protection of the phosphide in the preparation. The silicon-organic compound is used within a range of about 0.1% to about 3.0%, preferably 0.2% to 0.5%, by weight of the final pesticide composition.

Other objects and advantages of this invention will become apparent from the following description wherein are set forth, by way of example, certain embodiments of this invention and from the claims which are part of this disclosure.

DETAILED DESCRIPTION OF THE PREFERRED EMBODIMENTS

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention.

In general, the pesticide of the present invention comprises hydrolyzable phosphide particles and an additive which renders the pesticide liquid phase water repellent but permits free access of gaseous phase water to the phosphide particles. The additive is a silicon-organic compound having at least one reactive moiety suitable for reacting with and binding to reactive sites present in the composition, forming suitable reaction partners for reactive moieties of the silicon-organic compound to form a hydrophobic reaction product bonded to particles of the composition and protecting the composition against too violent reaction with liquid water. The reactions by which the hydrophobic reaction product is formed, according to our present understanding are mainly condensation type reactions, whereby the reactive moiety is split off and the broken linkage of the silicon-organic group becomes available for bond formation. The term "moiety" is used in this specification as a generic term for individual entities within a molecule, whether composed of a single atom or a group of atoms and regardless of the manner in which such entity is linked to the remainder of a single or complex molecule. Thus, whilst the term would include radicals, it is no longer correct in strict modern usage to employ the term "radical" as a synonym of "moiety".

The phosphide may be any phosphide which releases phosphine upon hydrolyzation or reaction with water. Normally, hydrolyzable technical grade metal phosphides contain substantial quantities of metal oxides and also small quantities of metal-bonded hydroxy groups, especially near or on the surface of particles, which are the nonphosphine reaction product of the phosphide and water, and which can play a special role as explained further below. Suitable phosphides are the metal phosphides of aluminum, calcium, magnesium or mixtures thereof. A preferred phosphide is a technical grade aluminum phosphide which contains in the nature of about 81% by weight aluminum phosphide, about 19% by weight aluminum oxide and less than about 1% by weight hydroxy groups calculated as aluminum hydroxide mostly situated on the surface of the aluminum phosphide particles.

The silicon-organic compound, in particular has a plurality of silicon atoms with at least one reactive moiety bound directly to one of the silicon atoms, as compared to conventional silicones used in producing metal phosphide pesticides having no reactive moiety. More specifically, the silicon-organic compound is comprised of molecules, each molecule may be identical or vary according to the limitations described herein. Each of the molecules has a plurality of structural units which in turn have one silicon atom per unit. Adjacent structural units are joined by an oxygen atom which is also bonded directly to the adjacent respective silicon atoms. All bonds of each silicon atom not occupied by oxygen or by the reactive moiety or moieties are filled by a low molecular weight alkyl or aryl radical, especially ethyl or phenyl and preferably methyl. (As used herein, low molecular weight refers to a molecular weight of 150 or less).

The reactive moieties of the silicon-organic compounds are split off when such compounds react with reactive sites representing suitable reaction partners in accordance with generally accepted reaction principles.

Thus, the reactive moieties of one or more silicon-organic molecule can serve as "reactive sites" in reaction with the reactive moieties of one or more other identical or different silicon-organic molecules to result in cross-linking or condensation-polymerisation and the formation of a fine network of water-repelling interlinked silicon-organic molecules extending over and bonded to the treated surfaces. This type of reaction may involve an interaction of atmospheric oxygen or even water vapour to form oxygen bridges between the cross-linked silicon atoms in a manner known in silicone chemistry. This hydrophobation mechanism is not limited to any particular chemical composition of the surfaces to which the silicon-organic compound is bonded. However, the presence in the chemical composition of such surfaces of amino groups or other groups (in particular basic groups) which catalyze the reaction can promote the formation of this type of bonded, cross-linked silicon-organic product.

The reactive moieties of the silicon-organic compounds are also known to react directly with moieties which have been found to occur on the surfaces of particles which are part of preferred pesticidal preparations, such reactions resulting in surface compounds directly chemically bonded to such surfaces. The most important of such moieties which can serve as reactive sites provided by the treated surfaces themselves are hydroxy moieties. Silicic acid which is frequently incorporated in small quantities up to about 2% by weight, but usually not more than 1% in metal phosphide preparations has hydroxy groups which readily react with reactive moieties of silicon-organic compounds as follows:

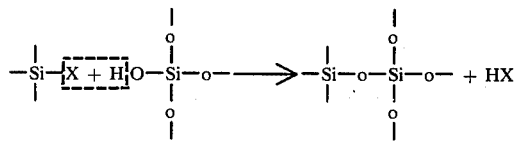

wherein X is the reactive moiety of the silicon-organic compound.

This reaction which is a condensation reaction can be employed to hydrophobise the silicic acid content of such preparations. More important, however, it is now realised by the applicants that similar hydroxy groups occur on the surfaces of metal phosphide particles, e.g., aluminum phosphide particles. These hydroxy groups offer themselves to an analogous hydrophobing condensation reaction:

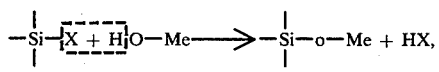

wherein Me is a metal atom of the metal phosphide particle. This type of direct chemical bonding of the hydrophobic silicon-organic groups to the metal surfaces is in line with the observation that the phosphide particles hydrophobised in accordance with the invention retain their hydrophobic properties until the hydrolytic decomposition of the particles during the use as a fumigant has reached an advanced stage.

The phosphorus atoms of metal phosphides, which are highly reactive and are readily hydrolised off in the form of phosphine, can probably serve as "reactive sites" for the purposes of the hydrophobing reaction in certain conditions. However, in the preferred reaction conditions still to be described these phosphorus atoms do not appear to play an important direct role in the case of aluminum phosphide. This is an advantage, since the comparatively small amounts of phosphorus which might otherwise have been used up in the hydrophobing reaction, remain available for generating phosphine in the use of the product as a pest control agent.

The comparatively large numbers of oxygen atoms present in the form of metal oxides in technical grade hydrolisable metal phosphides could in certain circumstances serve as "reactive sites" for the hydrophobing reaction. However, in the preferred treatment conditions these oxygen atoms are not observed to play any important part.

The aforegoing is not intended to state exhaustively all conceivable possibilities of "reactive sites", since these may depend on the ingredients of a particular preparation in the reactivity of the particular silicon-organic compound and the specific reaction conditions.

Generally speaking, the reactions of the said reactive moieties with appropriate reactive sites are promoted by heat and/or catalysis. Convenient temperatures elevated above ambient temperature for promoting the reaction are within the range of 80° to 200° C. and more preferably from 110° to 150° C., although variations outside these limits are possible to suit specific ingredients of a preparation. The reaction can also be promoted or catalysed by the maintenance of basic conditions which may be due to basic ingredients of the preparation subjected to treatment or to basic catalysts specially added. Catalytically effective are compounds such as ammonia, ammonium compounds (e.g. ammonium carbamate or carbonate) and amine compounds and mixtures or combinations of such compounds. In order to be effective, amounts from about one to five times by weight the amount of silicon-organic compound are normally sufficient.

Suitable catalysts for promoting the reaction include metal organic catalysts, preferably used in amounts of about 1% to about 10% by weight based on the silicon-organic compound used. Examples of such catalysts are organic compounds of lead, zinc, zirconium, cobalt, tin (usually in its stannic form) and titanium, especially zirconium butoxide, dibutyl stannic dilaurate and di-n-octyl stannic maleinate and the obvious equivalents thereof.

Large numbers of silicon-organic compounds are known in the literature having reactive moieties capable of undergoing the type of reaction employed in the hydrophobing treatments herein contemplated. Examples of known reactive moieties include halogens, hydroxy groups and $OR_1$, wherein $R_1$ is a low molecular weight alkyl group. Not all of these compounds are at present available commercially at reasonable cost. The optimum conditions for employing the different compounds obviously differ in a manner readily understood by those skilled in the art. Moreover, the choice can be affected by the composition to be treated and the particular components of a composition which are to be rendered hydrophobic. The selection can be made in the light of the known characteristics of the silicon-organic compound, the effect desired and the available manufacturing facilities by simple routine laboratory testing.

For various reasons (including ready availability at reasonable prices, ease of handling, good reactivity under convenient conditions) the preferred reactive moiety is hydrogen.

In particular embodiments the silicon-organic compound has the following general formula:

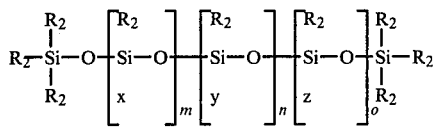

wherein each of the $R_2$ moieties preferably stands for a low-molecular weight alkyl group and especially a methyl group, or less preferably an aryl group, and especially the phenyl group; the moieties x, y, z represent either the previously mentioned $R_2$ moiety or hydrogen, however, all x, y and z moieties may represent hydrogen only or they may be different, that is some may represent hydrogen and the remainder $R_2$ moieties, in addition, at least one x, y or z must represent hydrogen; n, m, o denote whole numbers whose total ranges from 10 to 1000, preferably from 20 to 100. Whenever x, y and/or z represent hydrogen, they also thereby represent the reactive moiety or moieties of the silicon-organic compound.

In a particular embodiment each $R_2$ represents the same moiety and also preferably $R_2$ represents the methyl group. This preferred silicon-organic compound is in general referred to as a methylhydrogenpolysiloxane (it is also known as a polymethylhydrogenpolysiloxane, a polymethylpolyhydrogenpolysiloxane). It can also be described as a hydrogen silicone oil, in other words a kind of silicone oil. Methylhydrogenpolysiloxanes in the form of a low-viscosity oil are especially beneficial to the formation of the final pesticide, as the oil is easy to apply to the phosphide particles as will be discussed hereinafter without pretreatment such as melting. The preferred silicon-organic compounds at 70° F. have a viscosity of about 10 to 1000 centipoise (cp), more preferably less than 200.

It is speculated that the silicon-organic molecules form a "fishnet" effect on the treated surfaces, e.g. of the phosphide particles and that the $R_2$ radicals on each of the methylhydrogenpolysiloxane molecules in conjunction with the $R_2$ radicals on adjacent such molecules form a barrier to droplets of liquid phase water which are held together by surface tension, but allow passage therein-inbetween of individual water molecules in a gaseous state. Therefore, while the methylhydrogenpolysiloxane when used in large amounts can produce a thick effective layer thereof on the surface of the phosphides, only a light coating of the methylhydrogenpolysiloxanes in which the individual molecules are spread apart and have molecular discontinuities therebetween, but are still close enough together to form the above discussed barrier to liquid water, is sufficient for producing the desired effect. The method of operation of the silicon-organic compound is based on generally accepted principles relating to the hydrophobic effect of such compounds. Strong credence is lent thereto by the fact that only a very small amount of the silicon-organic compound used in conjunction with the phosphide particles will produce the desired liquid water repellent results. It should also be noted, that according to this theory the silicon-organic compound changes form after reaction with the hydroxides on the surface of the phosphide particles and that thereafter the reactive moiety is no longer bound to the remainder of the reacted silicon-organic molecule.

As discussed previously, the silicon-organic compounds react with and thus form stable reaction products or compounds with hydroxides present. On the surface of the phosphide particles hydroxy groups are present due to a portion of the phosphide being unavoidably hydrolyzed by atmospheric moisture. Ideally these hydroxy groups represent a very small, sometimes almost unmeasurable, amount. When these hydroxy groups react as postulated above, the resulting novel reaction products will have the following general formula:

$$Me—O—R_3$$

wherein Me represents the metal of the phosphide particle and $R_3$ represents a silicion-organic compound moiety remaining after removal of the reactive moiety therefrom, in the preferred case the reactive moiety being hydrogen. These reaction products are generally bound to the phosphide particles at the point whereat the hydroxy group was originally located and are thus randomly aligned on the surface of the phosphide particle, so as to shield the particles behind the outwardly directed methyl or like groups, thereby creating the liquid phase water repelling effect desired.

To summarise one aspect thereof, the present invention provides as novel products, useful in pest control, particles of hydrolizable phosphides of metals comprising bonded to their surfaces hydrophobic compounds which are the product of reaction between reactive sites on the surfaces of the particles and a silicon-organic compound having a moiety which is reactive with said sites.

Because the binding of the reacted silicon-organic compound generally positions the reaction product favourably on the particles and retards the removal of the reacted silicon-organic compound therefrom by "creep" or other phenomenon, it is therefore preferred that substantially all of the silicon-organic compound be thus bound to the surfaces of the phosphide particles. This results in the most direct and therefore a particularly effective protection of the phosphide particles against violent reaction with liquid water. Moreover, this protection persists for an appreciable time after the decomposition of the composition due to moisture has commenced.

However, an indirect protective effect is also attained if other ingredients of the preparation are rendered hydrophobic by the reaction of the silicon-organic compound. The hydrophobation of the additive silicic acid has already been referred to. In some manufacturing conditions it may be particularly convenient to hydrophobise such additives. For example, urea, a desirable ingredient in pesticidal metal phosphide compositions, is readily hydrophobised by the silicon-organic compounds.

It may be convenient to apply the hydrophobic treatment to a premix of metal phosphide particles and other ingredients in which case the other ingredients as well as the metal phosphide are rendered hydrophobic and then contribute to the water repellancy of the preparation as a whole.

For example, if a mixture comprising metal phosphide and urea is treated reactively with the silicon-organic compound, it is found that the urea is rendered hydrophobic by the reaction of a part of the silicon-organic compound. This hydrophobation of the urea contributes to the water repellancy of the preparation as a whole. It also delays the dissolution of the urea when brought into contact with liquid water. This protective effect is of shorter duration than that resulting from the direct hydrophobation of the phosphide particles, for which reason it is preferred to substantially confine the treatment to the phosphide.

It is especially surprising, that only a very small amount of a silicon-organic compound is necessary to make the final pesticide containing the phosphides powerfully liquid phase water repellent. To achieve similar liquid phase water repelling effects by use of normally used silicones without reactive groups requires amounts 10 to 30 times larger than is required of the present silicon-organic compounds. For other solid hydrophobic substances amounts up to 100 times larger are needed.

It has been shown that use of 0.2% to 0.5% of a silicon-organic compound, where the percentage is based by weight on the total final composition of the pesticide including the phosphides and other additives, will generally completely produce the desired liquid phase water repelling effect desired in the pesticide, yet the phosphide particles remain accessible to and reactive with gaseous phase water, as shown by experimentation therewith. Also smaller additions of only 0.1% produce final pesticides having satisfactory qualities in many cases. It is desirable only in exceptional situations to use greater than 0.5% of the silicon-organic compounds with the high range being about 3% based on weight on the composition of the final pesticide composition, as use of more than 3% may hamper processing of such final pesticides and is wasteful.

Depending upon the characteristics of the place of use of the pesticide, the phosphide may be made repellent to liquid phase water by use of the silicon-organic compound without any additional special measures or additives.

Where the pesticide will be used near inflammable material such as grain, it is preferable to include as a self-ignition inhibitor a thermally decomposing substance or blanketing agent in the pesticide which will produce an inert gas, such as ammonia or carbon dioxide, upon decomposition, which decomposition generally is due to a rise in ambient temperature and/or to a rise in temperature caused by hydrolyzation of the phosphide, thereby blanketing the relatively hot phosphine which is generated by the exothermic reaction of the phosphide with water vapour and thus suppress spontaneous ignition of the phosphine. The thermally decomposable substance is preferably selected from the group of ammonium containing compounds consisting of ammonium carbonate, ammonium carbamate, ammonium phosphates and mixtures thereof. Urea is a further desirable self-ignition inhibitor. The preferred self-ignition inhibitor is a mixture of ammonium carbamate and urea. The protective effect of urea is believed to be due to its endothermic decomposition in the presence of water at elevated temperature with the formation of $CO_2$ and ammonia.

Some of these ammonium compounds, especially ammonium carbamate which create basic conditions, can perform a secondary function to accelerate or catalyse the reaction of silicon-organic compounds with the reactive sites so that it is only necessary to form a simple mixture of the metal phosphides, silicon-organic compounds, and catalysing ammonium compound during the manufacturing process to obtain the desired hydrophobic qualities. After production is complete, the pesticide has the desired liquid phase water repellent qualities which tend to intensify for some time during subsequent treatment and storage.

In general, the method for producing the pesticides of the present invention comprises admixing a powder comprising a particulate or comminuted hydrolysable phosphide and a silicon-organic compound as described above. The silicon-organic compound is preferably a liquid or oil, preferably of low viscosity, and is stirred or otherwise mixed with the powder particles thereby wetting and coating the surface thereof. Also, the silicon-organic compound preferably totally or substantially as described above, reacts on and is bonded to the surfaces of the phosphide. This reaction may involve direct chemical bonding of the particle surface at the molecular bonding site of the reactive moiety of the silicon-organic compound. The reactions which result in the hydrophobation of particles of the preparation may also include cross-linkage reactions between molecules of the silicon-organic compound. Phosphide particles so treated have the characteristics of being liquid water repellent yet accessible to and reactive with water in a vapour state.

The reactions of the silicon-organic compound are promoted or catalyzed by elevated temperatures, basic conditions, ammonia, ammonium and amine compounds and certain metal organic compounds. In particular, this reaction is promoted by temperatures in the range of from about 80° to about 200° C., with the preferred reaction temperature occurring between the range of 110° to 150° C., as was previously stated. Thus, according to this method, temperatures in the above ranges can be advantageously used to promote the reaction. When an elevated temperature is used to promote this reaction, it may be preferred that the spontaneous ignition suppressing substance or blanketing agents not be added to the mixture until the heating process is complete, since the elevated temperature will tend to prematurely thermally decompose these blanketing agents.

Metal organic compositions or compounds, especially such compounds of lead, zinc, zirconium, cobalt, tin, titanium and mixtures thereof, as previously stated also catalyze the reaction of the silicon-organic compound with the reactive sites and can be used in the production method of the preparation. Thus, these metal organic compounds are used in particular method embodiments of this invention. Although these metal organic compounds can be added independently to the admixture of phosphide particles and the silicon-organic compound, it is preferred that they be premixed with and thus added with the latter. Particularly effective metal organic compound catalysts are zirconium butoxide, dibutylstannicdilaurate, di-n-octylstannicmaleinate, and mixtures thereof. The metal organic catalysts are normally used in a range from about 1% to about 10% by weight of the silicon-organic compound.

Ignition inhibitors which create a basic environment, which liberate ammonia, ammonium compounds and amines are also effective as a catalyst to the hydrophobising reactions of the silicon-organic compound and thus are effective in the methods disclosed herein. These self-ignition inhibitors may be added at various steps during the method of compounding the pesticide as will be discussed hereinafter. Blanketing agents such as ammonium carbonate and ammonium carbamate are especially well suited for this purpose as they are often already being added to the composition. Other ammonium and amine compounds which yield a basic reaction are also well suited for this purpose, as is ammonia. Some of these basic compounds such as triethylamine require a solvent, such as dichloromethane, for proper dispersal within the pesticide composition. A solvent when it is used for this purpose is allowed to substantially evaporate from the composition before the pesticide is ready for use. In general, larger amounts of the basic compounds are required as compared to the metal organic compounds to catalyze the hydrophobising reactions of the silicon-organic compound. Ranges of the basic compounds suitable for catalyzing this reaction are from about 0.1% to about 3.0% by weight of the final pesticide disregarding any solvent used therefor; of course, when the blanketing agents are used for this purpose, larger quantities of such agents may be used without harmful effects. In addition, ammonia released by the blanketing agents upon decomposition thereof also tends to catalyze this reaction even after being volatilised.

As was previously dicussed, the self-ignition inhibitors such as ammonium carbonate, ammonium carbamate, urea, or mixtures thereof, are optional depending upon the proposed usage of the final pesticide composition. These self-ignition inhibitors, when used, normally range from about 10% to about 50% by weight of the final pesticide composition. The self-ignition inhibitors also are normally in a powdered, granulated, or particulate form and may be added to the pesticide composition at the time when the phosphide and silicon-organic compound are admixed and/or mixed therewith at a later time. There are advantages associated with both a method of adding the self-ignition inhibitor to the initial admixture or a method of adding later. The major advantages of adding the self-ignition inhibitor to the initial admixture are, as was previously discussed, that many of the blanketing agents are basic and thus tend to catalyze the desired reactions of the silicon-organic compounds and such an initial addition tends to simplify the manufacturing process. The advantage of adding the self-ignition inhibitors at a time later than the initial admixing derives from the fact that the silicon-organic compounds are generally expensive relative to the other components of the pesticide, therefore it is desirous to use as small a quantity of the silicon-organic compound as will create the desired liquid repelling effect; in general a smaller quantity of silicon-organic compound is required to coat just the phosphide than would be required to hydrophobise both the phosphide and the self-ignition inhibitor to achieve the same degree of protection of the final preparation. Hence, although it is easier to cogrind the phosphide and the self-ignition inhibitor together before addition of the silicon-organic compound, so doing generally requires a greater quantity of the silicon-organic compound than is required when the silicon-organic compound is added to the phosphide particles alone.

In one particular method embodiment of the invention both of the addition advantages discussed above are exploited. This is accomplished by adding a portion of a catalytically effective ignition inhibitor into the initial admixture of the phosphide and the silicon-organic compound, which may also be done in combination with an elevated temperature, thereby catalyzing the hydrophobising reaction. The remaining portion of the self-ignition inhibitor is added after the catalyzed reaction is substantially complete and/or the silicon-organic compound treated phosphide particles have cooled to a point below that whereat the self-ignition inhibitor will thermally decompose. Suitable amounts of the catalyzing self-ignition inhibitor, preferably ammonium carbamate, for catalyzing the desired reaction of the silicon-organic compound are in the range of from about 0.5% to about 3% by weight of final pesticide composition and can be added to and milled with the phosphide. Total amounts of the self-ignition inhibitor are generally in the range of about 10% to about 50% by weight of the final pesticide composition, depending upon the desired end use of the pesticide and sufficient parts are added later, as discussed above, to provide these total percentages. It should be noted that final parts of the self-ignition inhibitor in the pesticide composition may be less than the total added, since some may decompose during production. Normally the self-ignition inhibitor, both basic and non-basic components, is present in the range from about 20% to about 35%, and preferably 30%, by weight of the final pesticide. The remaining portion of the self-ignition inhibitor not part of the initial addition is normally added to the pesticide composition after the silicon-organic compound has substantially completely reacted and bound to the phosphide particles. In this manner the silicon-organic compound is used more economically by not coating all of the blanketing agent. It has also been found that when the silicon-organic compound is used to treat only the phosphide or the phosphide in combination with only a small amount of the self-ignition inhibitor, the flow and pressing properties of the particles developed thereby are also substantially improved as compared to using an equivalent amount of the silicon-organic compound to treat a prior combination of the phosphide and the total self-ignition inhibitor.

The final pesticide composition therefore comprises silicon-organic compound treated particles of hydrolyzable phosphides and, when used, particles of the self-ignition retardant mixed therewith. For ease in dispensing, the pesticide composition is normally moulded or pressed into a tablet form, however, use of the preparation in powder form, subdivided into portions, each portion being individually enclosed in a pocket which is impervious to the powder, whilst permitting the access of atmospheric moisture to the powder, e.g. in small bags or sachets, pervious to moisture but preferably also repellent to liquid, is also suitable. In order to reduce degradation of the final pesticide product upon contact with atmospheric moisture and to insure the safety of the parties handling the pesticides, the tablets or bags are normally sealed in an air-tight container until use thereof.

In use the tablets are removed from the sealed containers thereof and selectively deposited in the areas or bulk materials to be fumigated thereby. Normally atmospheric humidity is sufficient to release the phosphine from the tablets. Since the tablets have a substantial degree of porosity to moisture in a gaseous phase, no bursting agent is required to initiate the phosphine producing hydrolyzation process. In common with other metal phosphide compositions containing ammonium carbamate, the compositions in accordance with the present invention, on being exposed to the atmosphere, liberate $CO_2$ and ammonia due to the decomposition of the ammonium carbamate to form a blanketing gas which inhibits self-ignition of phosphine gas simultaneously generated by the hydrolising effect of atmospheric moisture on the metal phosphide. For the first few hours the rate at which the tablets lose weight due to the decomposition of the carbamate is usually so high in relation to the rate at which the phosphide is hydrolized that the weight percentage of hydrolizable phosphide of the exposed tablet may remain almost constant for several hours and may even increase temporarily. This may happen in spite of the fact that the rate of actual phosphine generation may be very nearly constant for a major part of the exposure, virtually from the beginning thereof.

The safe placing of the compositions in an environment to be fumigated is possible if the normal precautions are observed. Persons working in such environment should leave or don gas masks before the phosphine concentration in such environment reaches a dangerous level.

In producing a tablet or pellet wherein the ingredients are pressed or moulded, it is useful to include a tableting aid of inert inorganic materials such as tricalciumphosphate, graphite, or silicic acid to assist in the tablet forming process. The hydroxy groups of silicic acid are known to react with reactive silicon-organic compounds as described further above. Finely divided silicic acid is sometimes added in small amounts to the metal phosphide powder to serve as a tableting aid. If present during the reaction of the silicon organic compound, the surfaces of the silicic acid particles will also be rendered hydrophobic by reaction with the silicon-organic compound. The resulting hydrophobic silicic acid particles can contribute to the hydrophobic properties of the composition as a whole. However, the hydrophobic effect of the silicon-organic compound is more effectively and economically utilised if such compound is applied directly to the surfaces of the metal phosphide particles. Accordingly it is preferred for the metal phosphide particles to be subjected to the hydrophobic treatment before any silicic acid tableting aid is added.

A particularly effective pesticide tablet compounding composition according to the present invention thus includes the following ingredients:

| Parts by weight of total pesticide | | |
|---|---|---|
| range | preferred | Ingredient |
| 89–56 | 68.5–69.5 | technical grade aluminum phosphide (being about 81% by weight actual aluminum phosphide and about 19% by weight aluminum oxide and having less than 1% hydroxy groups mostly upon the surface thereof) |
| 0.1–3.0 | 0.5 | methylhydrogenpolysiloxane |
| 5–25 | 20 | urea |
| 5–15 | 10 | ammonium carbamate |
| balance | up to 1 | tableting aid |

The following examples are designed to explain various features of the invention and are not intended to restrict the scope thereof:

EXAMPLE 1

70 parts of technical grade aluminum phosphide were finely ground and mixed with 10 parts of finely pulverized ammonium carbamate and 19.5 parts ground urea.

During the above mixing, 0.5 parts of methylhydrogenpolysiloxane with a viscosity of about 15 cp were added. The total mix time was 33 minutes. A free-flowing powder was obtained, which could be pressed into tablets without the addition of any other substances.

The qualities of tablets produced from the product according to this example are shown in Tables 1 and II. Tablets made according to Example 1 are also compared with conventional tablets in Tables 1 and II.

EXAMPLE 2

99 parts technical grade aluminum phosphide were intimately mixed in a mixer with 0.9 parts methylhydrogenpolysiloxane for 15 minutes. Then, 0.1 parts zirconium butoxide as a catalyst, were added and mixed for an additional 15 minutes and stored in a hopper for several hours.

A dust-free, free-flowing, liquid phase water repellent but gaseous phase water reactive product was thereby obtained.

EXAMPLE 3

To 98 parts aluminum phosphide, which was produced through thermal reaction between aluminum and phosphorus, were coarsely mixed 2 parts of methylhydrogenpolysiloxane as soon as the phosphide had cooled down to about 160° C., and the mixture was then ground. When, after additional cooling after several hours, the mixture had reached ambient temperature, it showed good liquid phase water repellent qualities but readily reacted with gaseous phase water when exposed to an average natural atmosphere containing atmospheric moisture.

EXAMPLE 4

The conditions and quantities as in Example 2 were repeated except that 0.1 parts of triethylamine dissolved in 9 parts dichloromethane were used on a catalyst. After 1 to 2 hours and evaporation of the solvent, dichloromethane, a freely flowing phosphide pesticide with the characteristic desired properties with regard to water resulted.

TEST 1

70 parts of the hydrophobic phosphide mixture produced according to examples 2 (or 3 with the same results) were mixed with 20 parts of urea and 10 parts of ammonium carbamate and then pressed into tablets having an 18 millimeter (mm) diameter.

They were compared to tablets of the same chemical composition except that the phosphides in the comparative tablet were untreated by methylhydrogenpolysiloxanes. To demonstrate the hydrophobic qualities a drop of water was placed on the tablet surfaces.

While the untreated tablet reacted immediately with the water, which reaction was substantially violent and visible with the reaction going to completion in a relatively very short period of time, the drop remained on the surface of the treated tablet for a substantially longer period of time. Only after 10 minutes did a slow reaction start in the treated tablet, which had not gone to completion even after 30 minutes.

An identical tablet, except that the methylhydrogenpolysiloxane is replaced by an identical amount of ordinary, non-reactive methyl silicone oil, reacts almost as violently and rapidly with a drop of water as does the untreated tablet. To a person skilled in the art, this difference in performance is a fundamental one and is immediately apparent. It demonstrates a fundamental and far-reaching difference between the effects of the two classes of silicon-organic compounds.

TEST 2

Table I illustrates by use of experimental data the effect of the invented use of the silicon-organic compound, here being methylhydrogenpolysiloxane. In the test the average phosphine released upon contact with liquid phase water at 20° C. is recorded for several tablets containing metal phosphides and various other ingredients, having compositions as shown in Table I, each tablet having a total weight of 3 grams (g).

In order to measure the amount of phosphine that was released, 250 milliliter (ml) volumetric measuring cylinders were filled with water. The cylinders were placed with their openings downward into a water filled container so as to exclude all air from the tubes which had been filled with water. A tablet according to the compositions in Table I with hydrolyzable phosphides therein was placed underneath each of the volumetric cylinders, so that the gas released by reaction with and into the water could be measured in ml. with respect to the time elapsed. The smaller the amount of gas which escapes per unit time, the stronger the relative liquid phase water repellent effect. It is believed that the reaction which occurred in tablet Composition I, according to the present invention, was due to reaction with water in the gaseous state which vaporized from the water in the liquid state.

TABLE I

| | Released phosphine gas in ml after | | | |
|---|---|---|---|---|
| | 5 min. | 10 min. | 30 min. | 60 min. |
| Composition I | | | | |
| (made according to Example 1) | | | | |
| 70 & technical AIP | 10 | 15 | 42 | 95 |
| 10% ammonium carbamate | | | | |
| 19.5% urea | | | | |
| 0.5% methylhydrogenpolysiloxane (150 cp) | | | | |
| Composition II | | | | |
| 70% technical AIP | 40 | 90 | 200 | 250 |
| 10% ammonium carbamate | | | | |
| 19.5% urea | | | | |
| 0.5% methyl-silicone oil (100 cp) (without a reactive group) | | | | |
| Composition III | | | | |
| 70% technical AIP | 12 | 20 | 150 | 250 |
| 10% ammonium carbamate | | | | |
| 10% urea | | | | |
| 10% aluminum stearate | | | | |

While Composition I demonstrates strong hydrophobic effectiveness against liquid phase water since the water in the cylinder was not completely displaced by phosphine within the test period, this composition has an additional important advantage since the finished pesticide composition has a very high water-vapour reactivity. Therefore the release of phosphine is not impaired nor is there a sudden reaction and release thereof, but rather a controlled release which continues at a steady and continuous rate as the phosphide reacts with water vapour. Because of the apparent excellent water vapour permeability of the hydrophobic reaction product on the particles, no so-called bursting substances are necessary, as are required for conventional hydrophobic phosphine pesticides according to U.S. Pat. No. 3,132,067. Composition II comprising the phosphide treated with silicone oil without a reactive group and Composition III which used a conventional type of hydrophobizing material, did not exhibit the controlled release desired and displayed by Composition I.

When compositions according to the invention, made as described in the examples are exposed to the atmosphere, the phosphine is substantially completely released within a relatively short time but does not tend to spontaneously ignite; this relatively short time during which the phosphine is active, is desirable since for pest control purposes a limited exposure time is very often required to avoid contact with humans or livestock.

TEST 3

The release of the phosphine from tablets produced according to the present invention was found to be not substantially slowed down by the silicon-organic compound as was the case with tablets made hydrophobic with 8% paraffin wax as shown in Table II.

For this test, the two types of tablets were simultaneously placed at 20° C. and 40% to 60% relative humidity in the open air and were examined at the noted specific time periods for their retained content of phosphine (in the form of phosphide) as compared with that amount originally present.

TABLE II

| | Relative Phosphine content (original content - 100%): | |
|---|---|---|
| Time elapsed | Invented tablet made hydrophobic according to Example 1. Relative phosphine content | Tablet made hydrophobic with 8% paraffin wax. Relative phosphine content |
| 0 hours | 100% | 100% |
| 4 hours | 92% | 94.1% |
| 6 hours | 73% | 81.1% |
| 16 hours | 20.2% | 45.3% |
| 24 hours | 8.9% | 40.8% |
| 48 hours | 3.0% | 9.5% |

The data demonstrate that the tablet treated with methylhydrogenpolysiloxanes released phosphine at a more continuous and faster overall rate over the test period than the paraffin wax treated phosphide and also reaches low concentration levels in a much shorter time span as compared therewith.

TEST 4

Powders of the two compositions according to Table I and one untreated but otherwise identical composition (i.e. containing no hydrophobing agent) were tested as follows:

All compositions had been stored in airtight containers for three days. 10 g portions of each composition were separately placed into beakers each containing 100 ml water (20° C.) and stirred thoroughly for 1 minute.

Immediately after said 1 minute each batch was filtered rapidly with suction. The filtrates were evaporated to dryness at 70° C. The residues were weighed. The residues consisted of urea (as confirmed by the biuret reaction) which had entered into aqueous solution during the period of mixing and filtering. The residue contained no ammonium carbamate, because ammonium carbamate is completely decomposed into $CO_2$ and ammonia during the evaporation.

The experiment was repeated and the following average results were recorded:

| Composition | % urea dissolved |
| --- | --- |
| I | 53.5 |
| II | 90 |
| Untreated | 92.5 |

During the test the following observation was made: Powder I showed no visible reaction with liquid water. The remaining two powders reacted violently with liquid water. The test leads to the following conclusions:
(a) The procedure according to Example 1 results in a part of the polymethylhydrogensiloxane being reacted to hydrophobise the urea.
(b) The resulting hydrophobic urea repels water sufficiently to delay the solution of the urea.
(c) The hydrophobic urea contributes to the hydrophobic protection of the preparation as a whole.
(d) The aluminum phosphide particles in the tablet are embedded in a matrix consisting of the hydrophobised urea and having admixed thereto ammonium carbamate.
(e) An important part of the polymethylhydrogen siloxane is reacted to hydrophobise the aluminum phosphide particles as such. This direct hydrophobic effect protects the phosphide more significantly and for a longer duration than does the hydrophobised urea. The effect persists when the urea is dissolved.

EXAMPLE 5

Seventy parts by weight of technical grade aluminum phosphide were milled together with 2 parts of ground ammonium carbamate. After milling, 0.5 parts of methylhydrogenpolysiloxane with a viscosity of approximately 15 cp were added and mixed thoroughly for 30 minutes and then stored in a hopper for one hour or more before entering into the next processing stage. Then, additional finely ground ammonium carbamate was added, such that the final composition contained 10 parts thereof, and also 19.5 parts of milled urea were stirred into the mixture until a homogenous, free flowing powder was achieved. The powder being liquid phase water repellent and gaseous phase water permeable. With no further additives, the powder could be pressed into a mould. In this manner, a portion of the ammonium carbamate was used to catalyze the hydrophobising reaction of the silicon-organic compound substantially wholly on the surface of the phosphide.

EXAMPLE 6

99 parts of commercial grade aluminum phosphide were thoroughly combined in a mixer with 0.9 parts by weight of methylhydrogenpolysiloxane for 15 minutes. Then, 0.1 parts of zirconium butoxide were added and mixed for an additional 15 minutes. The powder is stored in a hopper for one hour or more before use.

The result is a dust-free, free-flowing treated phosphide with the desired reactivity to gaseous water and repulsion to liquid water. 70.5 parts of this treated phosphide powder were then mixed with 10 parts of powdered ammonium carbamate and 19.5 parts of milled urea and pressed into tablets. In this manner the liquid phase water repelling effect is limited to the surfaces of the aluminum phosphide particles.

EXAMPLE 7

After a thermal reaction between aluminum and phosphorus and after the phosphide had cooled to about 160° C., 98 parts of the resulting aluminum phosphide were added to 2 parts of methylhydrogenpolysiloxane, the mixture was then mixed slightly and milled.

After additional cooling to ambient temperature the phosphide displayed marked liquid phase water repellent characteristics. The methylhydrogenpolysiloxane was bound to the phosphide surfaces as previously discussed.

70 parts of the methylhydrogenpolysiloxane treated phosphide were then mixed with 20 parts of urea and 10 parts of ammonium carbamate and pressed into tablets. In this manner the desired liquid water repellent characteristics are limited to the surfaces of the phosphide particles and are not transmitted to the spontaneous combustion suppressing additives, thereby optimising the use of the methylhydrogenpolysiloxane.

In addition, the powders of the pesticide produced according to this invention using methylhydrogenpolysiloxanes have very good free-flowing and mould separating qualities which facilitate the production of tablets therefrom. The otherwise frequent and troublesome sticking to pressing tools which normally occurs in the production of metal phosphide tablets is absent.

Another practical side effect is that powders of the present invention produce very little dust during further processing.

The examples have shown uses of functional organic-silicon additives. While any organic-silicon compound will basically coat the particles of the pesticide and thus render the phosphides contained therein at least somewhat liquid phase water repellent, the invention teaches using organic-silicon compound additives having an active or reactive moiety which will interact with reactive sites in the powder comprising the metal phosphides and thereby bond to the surfaces of the powder ingredients by chemical reaction.

It is to be understood that while certain forms of the present invention have been disclosed, it is not to be limited to the specific forms or examples here described. The teachings of the specific examples are intended to enable the person skilled in the art to apply these teachings in analogous manner to other embodiments contemplated by the specification.

The features described in the claims are to be considered a part of the present disclosure.

What is claimed and desired to secure by Letters Patent is:

1. In a phosphine producing pesticide composition comprising a mixture of a pesticidally effective amount of particles of a hydrolyzable metal phosphide and particles of a self-ignition inhibitor in an amount effective to protect the composition against spontaneous combustion of phosphine released from the composition, and which is hydrophobized so as to render the composition sufficiently repellant to liquid water to reduce the likelihood of spontaneous combustion upon contact therewith, the improvement wherein the composition is hydrophobized by a silicon-organic compound chemically bonded to the surface of at least the particles of the metal phosphide and present in an amount from about 0.1% to about 3% by weight of the pesticide composition.

2. A composition according to claim 1 wherein the silicon-organic compound is bonded to the surface of both the particles of the metal phosphide and the particles of the self-ignition inhibitor.

3. A composition according to claim 1 wherein the silicon-organic compound is bonded to only the surface of the particles of the metal phosphide.

4. A composition according to claim 1 in tablet or pellet form.

5. The composition according to claim 1 wherein the inhibitor is ammonium carbonate, ammonium carbonate, urea or a mixture thereof.

6. The composition according to claim 5 wherein the inhibitor is a mixture of ammonium carbonate and urea.

7. The composition according to claim 1 wherein the silicon-organic compound has structural units of the formula:

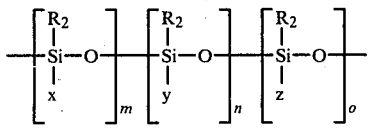

wherein each $R_2$ is a member of the group consisting of alkyl and aryl, each of a molecular weight of less than 150; at least one x, y and z is a hydrogen atom and the remainder are $R_2$; and m, n and o are whole numbers whose sum is between 10 and 1000.

8. The composition according to claim 1 wherein the metal phosphide is aluminum phosphide and the composition is hydrophobized by the reaction of methylhydrogenpolysiloxane on at least the surface of the aluminum phosphide particles.

9. The composition according to claim 8 wherein the methylhydrogenpolysiloxane has a viscosity at 70° F. of between about 10 centipose and about 1000 centipoise.

10. The composition according to claim 9 wherein the amount of methylhydrogenpolysiloxane is 0.2% to 0.5% by weight of said composition.

11. The composition according to claim 1 prepared from 89 to 56% by weight technical grade aluminum phosphide; 5 to 25% by weight urea; 5 to 15% by weight ammonium carbamate; and 0.1 to 3.0% by weight methylhydrogenpolysiloxane; and any balance, one or more tableting aids.

12. The composition according to claim 11, prepared from about 63.5%–69.5% by weight technical grade aluminum phosphide and 20% by weight urea, rendered hydrophobic by 0.5% by weight of the composition of methylhydrogenpolysiloxane; and 10% by weight ammonium carbamate.

13. The composition according to claim 1, wherein the metal phosphide is aluminum phosphide and the composition is hydrophobized by the reaction of a reactive silicon-organic compound on the surface only of the metal phosphide particles.

14. A composition according to claim 13, prepared from 89 to 56% by weight technical grade aluminum phosphide; 5 to 25% by weight urea; 5 to 15% by weight ammonium carbamate; and 0.1 to 3.0% by weight methylhydrogenpolysiloxane; and any balance, one or more tableting aids.

15. The composition according to claim 1 wherein the metal phosphide is aluminum phosphide and the composition is hydrophobized by the reaction of the reactive silicon-organic compound on the surfaces of a mixture of particles of the inhibitor and of the metal phosphide.

16. The composition according to claim 15 wherein the inhibitor comprises urea.

17. A composition according to claim 15, prepared from 89 to 56% by weight technical grade aluminum phoshide; 5 to 25% by weight urea; 5 to 15% by weight aluminum carbamate; and 0.1 to 3.0% by weight methylhydrogenpolysiloxane; and any balance, one or more tableting aids.

18. A process for the production of a pesticide composition according to claim 1 which comprises the steps of reacting on the surface of unhydrophobized particles of a metal phosphide, either prior to or after admixture thereof with self-ignition inhibitor, an amount from about 0.1 to 3.0% by weight of the composition of reactive silicon-organic compound effective to render the pesticidal composition hydrophobic.

19. A process according to claim 18 wherein the hydrophobized mixture of metal phosphide and inhibitor is thereafter formed into tablets or pellets.

20. A process according to claim 18 wherein the inhibitor is ammonium carbonate, ammonium carbamate, urea or a mixture thereof.

21. A process according to claim 20 wherein the inhibitor is a mixture of ammonium carbamate and urea.

22. A process according to claim 18 wherein the silicon-organic compound has structural units of the formula:

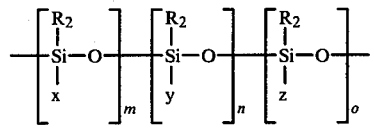

wherein each $R_2$ is a member of the group consisting of alkyl and aryl, each of a molecular weight of less than 150; at least one x, y and z is a hydrogen atom and the remainder are $R_2$; and m, n and o are whole numbers whose sum is between 10 and 1000.

23. A process according to claim 18 wherein a portion or all of the reactive silicon-organic compound is methylhydrogenpolysiloxane.

24. A process according to claim 23 wherein the methylhydrogenpolysiloxane has a viscosity at 70° F. of between about 10 centipoise and about 1000 centipoise.

25. A process according to claim 24 wherein the amount of methylhydrogenpolysiloxane is 0.2% to 0.5% by weight of said composition.

26. A process according to claim 18 prepared from 89 to 56% by weight technical grade aluminum phosphide; 5 to 25% by weight urea; 5 to 15% by weight ammonium carbamate; and 0.1 to 3.0% by weight methylhydrogenpolysiloxane; and any balance, one or more tableting aids.

27. A process according to claim 26 wherein the composition is prepared from about 63.5%–69.5% by weight technical grade aluminum phosphide and 20% by weight urea, rendered hydrophobic by 0.5% by weight of the composition of methylhydrogenpolysiloxane; and 10% by weight ammonium carbamate.

28. A process according to claim 18 wherein the reaction with the reactive silicon-organic compound is conducted only on the surface of the metal phosphide particles.

29. A process according to claim 28 wherein the composition is prepared from 89 to 56% by weight technical grade aluminum phosphide; 5 to 25% by weight urea; 5 to 15% by weight ammonium carbamate; and 0.1 to 3.0% by weight methylhydrogenpolysiloxane; and any balance, one or more tableting aids.

30. A process according to claim 18 wherein the reaction with the reactive silicon-organic compound is conducted on the surfaces of a mixture of particles of the inhibitor and of the metal phosphide.

31. A process according to claim 30 wherein the inhibitor comprises urea.

32. A process according to claim 30 wherein the composition is prepared from 89 to 56% by weight technical grade aluminum phosphide; 5 to 25% by weight urea; 50 to 15% by weight ammonium carbamate; and 0.1 to 3.0% by weight methylhydrogenpolysiloxane; and any balance, one or more tableting aids.

33. A process according to claim 18 wherein the reaction of the reactive silicon-organic compound is conducted in the presence of a catalyst for the reaction.

34. A process according to claim 33 wherein the catalyst is a metal organic compound.

35. A process according to claim 34 wherein the catalyst is employed in an amount from about 1% to about 10% by weight of the reactive silicon-organic compound.

36. A process according to claim 33 wherein the reaction is catalyzed by conducting the reaction under basic conditions.

37. A process according to claim 34 wherein the reaction is conducted in the presence of and is catalyzed by the ignition inhibitor.

38. A process according to claim 33 wherein the reaction is catalyzed by ammonium carbamate.

39. A process according to claim 38 wherein the catalyst is employed in an amount from about one to five times by weight the amount of the reactive silicon-organic compound.

40. A process according to claim 18 wherein the reaction is conducted at an elevated temperature.

41. A process according to claim 40 wherein the reaction is conducted at a temperature of 80° to 200° C.

42. A method of controlling pests in an environment susceptible to infestation by such pests which comprises exposing to water in that environment an amount effective to generate a pesticidally toxic amount of phosphine gas in that environment of a composition of claim 1.

43. A method according to claim 42 wherein the water is in the form of water vapor and the phosphine gas thus produced is introduced into and maintained in an environment susceptible to infestation by pests.

* * * * *